United States Patent [19]

Nishimura et al.

[11] 4,165,328

[45] Aug. 21, 1979

[54] PROCESS FOR SEPARATING 11-CYANOUNDECANOIC ACID, CYCLOHEXANONE AND ε-CAPROLACTAM

[75] Inventors: Kenji Nishimura; Haruhiko Miyazaki; Kenji Kuniyasu; Satoru Ono, all of Ube, Japan

[73] Assignee: Ube Industries, Ltd., Yamaguchi, Japan

[21] Appl. No.: 901,089

[22] Filed: Apr. 28, 1978

[30] Foreign Application Priority Data

May 4, 1977 [JP] Japan .................................. 52-50670
May 4, 1977 [JP] Japan .................................. 52-50671

[51] Int. Cl.² ......................................... C07C 121/407
[52] U.S. Cl. .............................. 260/404; 260/239.3 A; 203/29; 203/43
[58] Field of Search ................ 203/29, 39, 34, 35, 203/43, 47, 48, 49; 260/404, 586 R, 239.3 A

[56] References Cited

U.S. PATENT DOCUMENTS

| 3,217,027 | 11/1965 | Little | 260/404 |
| 3,970,677 | 7/1976 | Nishimura et al. | 260/404 |
| 3,994,942 | 11/1976 | Nishimura et al. | 260/404 |

FOREIGN PATENT DOCUMENTS

1266213  3/1972  United Kingdom ..................... 260/404

*Primary Examiner*—Wilbur L. Bascomb, Jr.
*Attorney, Agent, or Firm*—Miller & Prestia

[57] ABSTRACT

Disclosed is a process for separating 11-cyanoundecanoic acid, cyclohexanone and ε-caprolactam from a pyrolysis product obtained by pyrolyzing 1,1'-peroxydicyclohexylamine in the presence of steam at a temperature of 300° to 1,000° C. The pyrolysis product is first contacted with a mixture comprised of aqueous ammonia and at least one organic solvent selected from benzene, toluene and xylene, and the so prepared liquid is separated into the oily layer and the aqueous layer. On one hand, the oily layer is distilled to separate cyclohexanone therefrom. On the other hand, the aqueous layer is acidified to a pH of below 4.0 by adding thereto a mineral acid and maintained at a temperature of 40° to 100° C. to separate crude 11-cyanoundecanoic acid in molten form from the aqueous layer, and then, the separated crude molten 11-cyanoundecanoic acid is washed with hot water to extract ε-caprolactam therefrom.

8 Claims, No Drawings

PROCESS FOR SEPARATING 11-CYANOUNDECANOIC ACID, CYCLOHEXANONE AND ε-CAPROLACTAM

This invention relates to a process for separating 11-cyanoundecanoic acid, cyclohexanone and ε-caprolactam from a pyrolysis product of 1,1'-peroxydicyclohexylamine.

11-Cyanoundecanoic acid is of great use as a raw material for the production of nylon-12. ε-caprolactam and cyclohexanone are also of great use as raw materials for the production of nylon-6. Cyclohexanone may be used, in addition to in the production of nylon-6, in the production of 1,1'-peroxydicyclohexylamine, e.g., by reacting cyclohexanone with ammonia and hydrogen peroxide.

The preparation of 11-cyanoundecanoic acid by pyrolyzing 1,1'-peroxydicyclohexylamine is well known. For example, British Pat. No. 1,198,422 discloses the pyrolysis carried out at an elevated temperature in the range of from 300° to 1,000° C. in the vapor phase. German Patent Offenlegungsschrift No. 2,038,956 discloses the pyrolysis carried out at an elevated temperature while an inert gas such as steam is introduced in the reaction mixture. The pyrolysis product so obtained is usually pitch-dark or dark brown and contains 11-cyanoundecanoic acid and its isomeric compounds, cyclohexanone, ε-caprolactam, saturated and unsaturated carboxylic acids and nitriles, and cyclic imide.

In the production of 11-cyanoundecanoic acid by pyrolyzing 1,1'-peroxydicyclohexylamine, it is very much desired that the intended 11-cyanoundecanoic acid be efficiently separated from the pyrolysis product by rather simple purification procedures and with enhanced purity. It is also desired that the inevitably produced ε-caprolactam and cyclohexanone be efficiently separated from the pyrolysis product. However, it is difficult to efficiently separate the intended product of high purity by conventional simple purification procedures such as distillation and recrystallization.

For example, Japanese Patent Laid-open application No. 32,520/76 discloses the separation of 11-cyanoundecanoic acid, ε-caprolactam and cyclohexanone from the pyrolysis product of 1,1'-peroxydicyclohexylamine. According to this Laid-open application, cyclohexanone is first distilled off from the pyrolysis product and the residue product is dissolved in a solvent substantially insoluble in water and incapable of dissolving a salt of 11-cyanoundecanoic acid. Into this solution gaseous ammonia is introduced to form ammonium 11-cyanoundecanoate, followed by the separation of the ammonium salt so formed. Then, ε-caprolactam is extracted with water from the ammonium salt-separated residue solution and, finally, again extracted with an organic solvent from the aqueous extract. This separation procedure is not advantageous in the following points. First, 11-cyanoundecanoic acid contained in the pyrolysis product is partially subjected to thermal decomposition during the distillation for separating cyclohexanone, resulting in a reduction of the yield of 11-cyanoundecanoic acid and in an increase of the content of undesirable colored matters in the separated 11-cyanoundecanoic acid, i.e., an increase of the Hazen number of the separated 11-cyanoundecanoic acid. Secondly, ammonium salts of 11-cyanoundecanoic acid isomers inevitably crystallize out together with the intended ammonium salt of 11-cyanoundecanoic acid. But, when gaseous ammonia is blown into the solution, a part of cyclohexanone reacts with ammonia resulting in loss of cyclohexanone, and in increase of colored matters in the resultant crystallized product.

British Pat. No. 1,266,213 discloses the process for recovering 11-cyanoundecanoic acid from the pyrolysis product of 1,1'-peroxydicyclohexylamine, particularly from the pyrolysis product which is substantially free from cyclohexanone. This process comprises dissolving crude 11-cyanoundecanoic acid in aqueous ammonia and crystallizing out the ammonium salt of 11-cyanoundecanoic acid by cooling the solution. It is stated in this patent that cyclohexanone is recovered from the pyrolysis product by distillation, before the pyrolysis product is dissolved in aqueous ammonia. It is further stated therein that ε-caprolactam is separated, before the crystallization of the ammonium salt, by bringing the aqueous solution of the crude 11-cyanoundecanoic cyanoundecanoic acid containing ammonia into contact with an organic solvent such as chloroform, and then, by separating the organic solvent layer containing ε-caprolactam from the aqueous layer containing the 11-cyanoundecanoic acid.

The disadvantage in separating cyclohexanone by distillation is hereinbefore described as the first disadvantage with reference to Japanese Patent Laid-open Application No. 32,520/76. Moreover, chloroform used as the extraction solvent for ε-caprolactam is considerably soluble in an aqueous ammonia solution of 11-cyanoundecanoic acid. Due to the dissolved chloroform, ammonium salt of 11-cyanoundecanoic acid of a poor quality is crystallized out by cooling the raffinate.

It is, therefore, a main object of the present invention to provide a process for separating 11-cyanoundecanoic acid, cyclohexanone and ε-caprolactam from a pyrolysis product of 1,1'-peroxydicyclohexylamine, by which the respective ingredients can be efficiently separated and the intended 11-cyanoundecanoic acid can be obtained with high purity.

Other object and advantages of the present invention will be apparent from the following description.

In accordance with the present invention, there is provided a process for separating 11-cyanoundecanoic acid, cyclohexanone and ε-caprolactam from the product obtained by pyrolyzing 1,1'-peroxydicyclohexylamine in the presence of steam at a temperature in the range of from 300° to 1,000° C., which comprises the steps of:

contacting the pyrolysis product with a mixture comprised of aqueous ammonia and at least one organic solvent selected from benzene, toluene and xylene, followed by separation of the so prepared liquid into the oily layer and the aqueous layer;

distilling, on one hand, the oily layer to separate cyclohexanone;

acidifying, on the other hand, the aqueous layer to a pH of below 4.0, by adding thereto a mineral acid, and maintaining the acidified aqueous layer at a temperature in the range of from 40° to 100° C. to separate crude 11-cyanoundecanoic acid in molten form, and then;

washing the separated crude molten 11-cyanoundecanoic acid with hot water to separate ε-caprolactam therefrom.

The pyrolysis product used in the process of the invention is prepared by pyrolyzing 1,1'-peroxydicyclohexylamine at a temperature in the range of from 300° to 1,000° C. in the presence of steam and, if desired, a diluent such as benzene, toluene or xylene. The pyrolysis product contain 11-cyanoundecanoic acid, cyclohexanone and ε-caprolactam in amounts corresponding to from 50 to 60% by weight, from 10 to 20% by weight and from 10 to 20% by weight, respectively, of the weight of 1,1'-peroxydicyclohexylamine used. Besides these three ingredients, the pyrolysis product contains isomeric compounds of 11-cyanoundecanoic acid, saturated and unsaturated carboxylic acids and nitriles and cyclic imide, the total amounts thereof corresponding to from 10 to 20% by weight of the weight of 1,1'-peroxydicyclohexylamine used.

The pyrolysis product of 1,1'-peroxydicyclohexylamine is first contacted with a mixture comprised of aqueous ammonia and at least one organic solvent selected from benzene, toluene and xylene, and the liquid so prepared is separated into the oily layer containing a substantial part of cyclohexanone and the aqueous layer containing substantial parts of ammonium 11-cyanoundecanoate and ε-caprolactam. The amount of aqueous ammonia contained in the mixture is not particularly limited, but it is preferable that the ratio by mole of ammonia to the total acid compounds contained in the pyrolysis product be within the range of from 1:1 to 40:1, particulary from 2:1 to 10:1. Furthermore, the concentration of ammonium 11-cyanoundecanoate in the aqueous layer is also not particularly limited, but the concentration of ammonium 11-cyanoundecanoate is preferably in the range of from 5 to 30% by weight. When the concentration of ammonium 11-cyanoundecanoate is too low, cyclohexanone and other organic substances and colored matters are inevitably incorporated into the aqueous layer, and it becomes necessary to repeatedly wash the aqueous layer with an organic solvent. In contrast, when the concentration of ammonium 11-cyanoundecanoate exceeds the above-mentioned range, ammonium 11-cyanoundecanoate tends to crystallize out from the aqueous phase.

The contact of the pyrolysis product with a mixture of aqueous ammonia and the organic solvent or solvents may be carried out in any convenient manner. For example, a mixture of aqueous ammonia and the organic solvent or solvents may be added to the pyrolysis product after the completion of the pyrolysis reaction. Alternatively, in the case where the pyrolysis reaction is conducted in the presence of a diluent selected from benzene, toluene and xylene, only aqueous ammonia may be added to the pyrolysis product or gaseous ammonia may be blown thereinto.

The separation of cyclohexanone from the above-mentioned oily layer may be effected by distillation. That is, cyclohexanone can be efficiently separated from the solvent such as benzene, toluene and xylene, and by-products contained in the pyrolysis product, by utilizing the difference in boiling point between cyclohexaone and these ingredients.

The above-mentioned aqueous layer containing substantial parts of ammonium 11-cyanoundecanoate and ε-caprolactam is treated as follows. The aqueous layer is acidified to a pH of below 4.0 by adding thereto a mineral acid such as hydrochloric acid, sulfuric acid, nitric acid and the like, and maintained at a temperature of from 40° to 100° C., thereby to be divided into the upper layer predominantly comprised of a molten 11-cyanoundecanoic acid and the lower layer of an aqueous solution of an ammonium salt of mineral acid, containing ε-caprolactam. These two layers are separated from each other. The crude molten 11-cyanoundecanoic acid contains a minor amount of ε-caprolactam and, in order to remove ε-caprolactam therefrom, is washed with hot water. The washed molten 11-cyanoundecanoic cyanoundecanoic-cyanoundecanoic acid may be cooled to be solidified, pulverized and, then, dried to obtain a crystal of 11- acid.

The aqueous ammonium salt solution separated from the crude molten 11-cyanoundecanoic acid and the washing water collected after being used for washing the crude molten 11-cyanoundecanoic acid are combined with each other and, if desired, concentrated. ε-caprolactam may be removed from the combined aqueous solution by salting-out and/or extraction with an organic solvent. An organic solvent used for the extraction may be selected from those which are conventionally used for extracting ε-caprolatam, for example, toluene, xylene, acetic acid esters, trichlene, chloroform, dichloroethane and benzene.

By the process of the invention as described above, 11-cyanoundecanoic acid, cyclohexanone and ε-caprolactam can be separated with high recoveries from the pyrolysis product of 1,1'-peroxydicyclohexylamine. Furthermore, since the pyrolysis product is not exposed to a high temperature at the step of recovering 11-cyanoundecanoic acid from the pyrolysis product, the recovered 11-cyanoundecanoic acid is of enhanced purity and contains only extremely minor amounts of colored matters.

The recovered 11-cyanoundecanoic acid is usually comprised of 75% to 95% by weight of 11-cyanoundecanoic acid, 4% to 11% by weight of its isomeric compounds and 0.1% to 0.2% by weight of tarry materials. It has been heretofore rather difficult to completely remove the isomers of 11-cyanoundecanoic acid and tarry materials from the recovered 11-cyanoundecanoic acid. However, cyclohexane or n-hexane was found to be advantageous as the extraction solvent of 11-cyanoundecanoic acid because of its high extraction selectivity, i.e., in that in dissolves little or no tarry materials and colored matters. Furthermore, it now has been found that these impurities can be efficiently removed from the recovered acid by the process which comprises the steps of:

(a) extracting 11-cyanoundecanoic acid and the isomeric compounds thereof with cyclohexane or n-hexane from the recovered 11-cyanoundecanoic acid, and cooling the extracted solution to crystallize out only 11-cyanoundecanoic acid, followed by recovering the crystallized acid;

(b) from the mother liquor obtained by the step (a), extracting isomeric compounds of 11-cyanoundecanoic acid with aqueous ammonia, and then;

(c) recycling the raffinate obtained by the step (b), as an extraction solvent for 11-cyanoundecanoic acid and the isomeric compounds thereof.

The process of purifying the recovered 11-cyanoundecanoic acid, which comprises the above-mentioned three steps, will be described in more detail in the following.

Step (a):

The extraction of 11-cyanoundecanoic acid and its isomeric compounds with cyclohexane or n-hexane from the recovered 11-cyanoundecanoic acid is carried out preferably at a temperature of from 40° to 80° C. The extracted solution mainly contains 11-cyanoundecanoic acid and its isomeric compounds. The extraction residue containing impurities such as tarry materials and colored matters, is disposed of. The extracted solution is cooled to a temperature in the range of from 10° to 30° C., thereby to crystallize out only 11-cyanoundecanoic acid. Thus, 11-cyanoundecanoic acid of high purity and extremely reduced Hazen unit is obtained with high recovery. The mother liquor, after the above-mentioned extraction of 11-cyanoundecanoic acid, may be used cyclically as an extractant for extracting 11-cyanoundecanoic acid from the starting crude acid.

Step (b):

After the crystallization of 11-cyanoundecanoic acid in the above-mentioned step (a), the mother liquor is subjected to extraction by using aqueous ammonia as an extraction solvent for the removal of the isomeric compounds. The suitable extraction temperature varies depending upon the crystallization temperature in the step (a) and is usually in the range of from 0° to 70° C. The concentration of ammonia in the extraction solvent is preferably 2% to 28% by weight, and the amount of the extraction solvent is preferably 0.05 to 2 times in volume that of the mother liquor.

Step (c):

After the extraction of the isomeric compounds in the above-mentioned step (b), the raffinate predominantly comprised of cyclohexane or n-hexane is recycled as an extraction solvent for 11-cyanoundecanoic acid and its isomeric compounds in the above-mentioned step (a). A part of the raffinate may be used for washing the crystallized 11-cyanoundecanoic acid in the step (a).

The invention will be further described with reference to the following examples in which percents and parts are by weight unless otherwise specified.

Example 1

A toluene solution of 1,1'-peroxydicyclohexylamine was subjected to pyrolysis at a temperature of 500° C. in the vapor phase while steam was introduced into the gaseous feed. The pyrolysis product was comprised of:

11-cyanoundecanoic acid: 2.26 parts
ε-caprolactam: 0.59 part
cyclohexanone: 0.88 part
other by-products: 0.84 part
toluene: 3.88 part
water: 21.14 parts Gaseous ammonia was blown into the liquid pyrolysis product, and the liquid was separated into the oily layer (I) and the aqueous layer. The aqueous phase was passed through a multi-stage extraction tower provided with thirty perforated plates where the aqueous layer was contacted countercurrently with 12.22 parts of toluene, thereby to extract cyclohexanone from the aqueous layer. Thus, there were obtained the toluene solution (II) containing cyclohexanone and the aqueous raffinate. 4.58 Parts of a 20% aqueous sulfuric acid were added to the aqueous extraction residue to adjust the pH thereof to 3.0, keeping the aqueous raffinate at a temperature of 60° C., and the resultant product was separated into two layers, i.e., a crude molten free 11-cyanoundecanoic acid layer and the aqueous layer (III) containing a substantial part of ε-caprolactam. The crude molten 11-cyanoundecanoic acid layer still contained small amounts of ε-caprolactam and other by-products. The crude molten 11-cyanoundecanoic acid layer was passed through a twenty stage rotary disk extraction tower where the crude molten 11-cyanoundecanoic acid was contacted countercurrently with 40.13 parts of hot water to extract ε-caprolactam, whereby there were obtained 2.64 parts of molten 11-cyanoundecanoic acid and the collected washing water (IV). The molten 11-cyanoundecanoic acid was cooled to be solidified, pulverized and, then, dried to obtain a crystalline product containing 2.24 parts of 11-cyanoundecanoic acid. A one percent solution of the crystals exhibited a Hazen number of 48.

The above-mentioned oily layer (I) was mixed with the above-mentioned toluene solution (II), and the mixture was distilled to obtain 0.88 part of cyclohexanone. The above-mentioned aqueous layer (III) was mixed with the above-mentioned collected washing water (IV), and the mixture was subjected to extraction to obtain 0.54 part of ε-caprolactam.

Example 2

0.20 Part of a 20% aqueous sulfuric acid was added to a pyrolysis product of 1,1'-peroxydicyclohexylamine, having the same composition as that used in Example 1, to adjust the pH of the pyrolysis product to 3.0. 1.94 Parts of toluene were added to the acidified pyrolysis product and the mixture was separated into the oily layer and the aqueous layer (I). 24.73 Parts of an 4% aqueous ammonia were mixed with the oily layer, then allowed to separate into the oily layer (II) and the aqueous layer. The aqueous layer was passed through a multi-stage extraction tower provided with thirty perforated plates where the aqueous layer was contacted countercurrently with 13.73 parts of toluene to extract cyclohexanone from the aqueous phase and, thus, there were obtained the toluene solution (III) containing the cyclohexanone and the aqueous raffinate. 4.99 Parts of a 20% aqueous sulfuric acid were added to the aqueous raffinate to adjust the pH thereof to 3.0 and while keeping a temperature of 60° C., it was separated into a crude molten free 11-cyanoundecanoic acid layer and the aqueous layer (IV) containing a substantial part of ε-caprolactam. The crude molten 11-cyanoundecanoic acid layer was passed through a twenty stage rotary disk extraction tower where the crude molten 11-cyanoundecanoic acid was contacted countercurrently with 38.75 parts of hot water to extract ε-caprolactam, whereby there were obtained 2.64 parts of molten 11-cyanoundecanoic acid and the collected washing water (V). The molten 11-cyanoundecanoic acid was cooled to be solidified, pulverized and, then, dried to obtain a crystalline product containing 2.24 parts of 11-cyanoundecanoic acid. A one percent solution of the crystals exhibited a Hazen number of 46.

The above-mentioned oily layer (II) was mixed with the above-mentioned toluene solution (III), and the mixture was distilled to obtain 0.88 part of cyclohexanone. The above-mentioned aqueous layer (IV) was mixed with the above-mentioned collected washing water (V), and the mixture was subjected to extraction to obtain 0.54 part of ε-caprolactam.

Comparative Example 1

A pyrolysis product having the same composition as that used in Example 1 was distilled at a temperature of 130° C. to remove cyclohexanone therefrom. The distillation was continued until the charged pyrolysis product was reduced to one half in volume, while a part of the lower aqueous layer in the distillate was refluxed to the top of the distillation column. The distillation residue was subjected to liquid separation at a temperature of 60° C. to obtain a molten 11-cyanoundecanoic acid. The molten acid was washed with hot water, cooled to be solidified, pulverized and, then, dried to obtain a crystalline product containing 2.20 parts of 11-cyanoundecanoic acid. The crystal exhibited a Hazen number of 160 as measured in a one percent solution.

Example 4

This example illustrates a process of purifying the recovered 11-cyanoundecanoic acid from the pyrolysis product.

The recovered 11-cyanoundecanoic acid obtained by the procedure set forth in Example 1 was found to be comprised of:

11-cyanoundecanoic acid: 89.3 parts
isomeric compounds acid: 8.5 parts
other impurities: 2.2 parts, and posses a Hazen number of 50 as measured in a one percent solution.

Step (a):

100 Parts of the above-mentioned recovered 11-cyanoundecanoic acid were subjected to extraction by using as an extraction solvent 2,900 parts of cyclohexane at a temperature of 50° C., and then, the cyclohexane layer separated therefrom was cooled to 10° C. thereby to crystallize out 11-cyanoundecanoic acid. After separating the crystals by filtration, the crystals was washed with cyclohexane and, then dried. The amount of the crystals so obtained was 77.9 parts (yield=87.1%). The crystals exhibited as purity of 100% and a Hazen number of 50 as measured in a 25% solution.

The above-mentioned extraction-crystallization procedure was repeated five more different times. For each of the five repeated procedures, the same amount of the recovered 11-cyanoundecanoic acid was subjected to extraction wherein the mother liquor obtained by the preceding crystallization operation was used as the extraction solvent. The yield percentage, purity percentage and Hazen number (25% solution) of the 11-cyanoundecanoic acid crystal obtained by each of the five repeated extraction-crystallization procedures are shown as follows.

| Five repeated procedures | Yield (%) | Purity (%) | 25% Hazen number |
|---|---|---|---|
| 2nd | 95.9 | 100 | 45 |
| 3rd | 95.3 | 100 | 48 |
| 4th | 95.5 | 100 | 52 |
| 5th | 94.8 | 100 | 50 |
| 6th | 94.3 | 98.4 | 65 |

Step (b):

200 Parts of 5% aqueous ammonia were added at a temperature of 50° C. to 3,660 parts of the mother liquor obtained after the sixth operation in the above-mentioned step (a), whereby isomeric compounds of 11-cyanoundecanoic acid, accumulated in said mother liquor, were extracted therefrom.

Step (c):

The raffinate, after the extraction of the isomeric compounds in the above-mentioned step (b), could be again recycled as the extraction solvent mentioned in step (a).

What we claim is:

1. In a process for separating 11-cyanoundecanoic acid from the product obtained by pyrolyzing 1,1'-peroxydicyclohexylamine which product contains $\epsilon$-caprolactam in the presence of steam at a temperature in the range of from 300° C. to 1,000° C., the improvement which comprises the steps of:
    (a) contacting the pyrolysis product with a mixture comprised of aqueous ammonia and at least one organic solvent selected from benzene, toluene and xylene,;
    (b) separating the so prepared liquid into an oily layer and an aqueous layer;
    (c) acidifying said aqueous layer to a pH of below 4.0 with a mineral acid,
    (d) maintaining the acidified liquid at a temperature in the range of from 40° to 100° C. so as to obtain crude 11-cyanoundecanoic acid in molten form,
    (e) separating said crude 11-cyanoundecanoic acid from said liquid;
    (f) washing the crude molten 11-cyanoundecanoic acid with hot water to separate $\epsilon$-caprolactam therefrom.

2. A process according to claim 1 wherein the amount of the aqueous ammonia used is such that the ratio by mole of the ammonia contained in the aqueous ammonia to the total acid compounds contained in the pyrolysis product is within the range of from 1:1 to 40:1.

3. A process according to claim 2 wherein the ratio by mole of the ammonia to the total acid compounds is within the range of from 2:1 to 10:1.

4. A process according to claim 1 wherein the amount of the aqueous ammonia is chosen so that the resultant aqueous layer contains 5% to 30% by weight of 11-cyanoundecanoic acid.

5. A process according to claim 1 wherein the contact of the pyrolysis product with the mixture of aqueous ammonia and the organic solvent is effected by adding said mixture to the pyrolysis product.

6. A process according to claim 1 wherein the contact of the pyrolysis product with the mixture of aqueous ammonia and the organic solvent is effected by blowing gaseous ammonia into the pyrolysis product.

7. A process according to claim 1 wherein the washing water collected after washing the crude molten 11-cyanoundecanoic acid with hot water in step (f) is combined with a solution of an ammonium salt of mineral acid, and subjected to at least one separation treatment of salting-out and extraction with an organic solvent so as to separate $\epsilon$-caprolactam therefrom.

8. A process according to claim 1 including the step of purifying the washed 11-cyanoundecanoic acid by the steps of:
    extracting said 11-cyanoundecanoic acid with a solvent selected from the group consisting of cyclohexane or n-hexane, and cooling the extracted solution to crystallize out 11-cyanoundecanoic acid, followed by recovering the crystallized acid.

* * * * *

UNITED STATES PATENT AND TRADEMARK OFFICE
CERTIFICATE OF CORRECTION

PATENT NO. : 4,165,328
DATED : August 21, 1979
INVENTOR(S) : Kenji Nishimura et al It is certified that error appears in the above-identified patent and that said Letters Patent are hereby corrected as shown below:

Col. 2, line 18, "cyanoun-" should be deleted.

line 19, "decanoic" should be deleted.

line 40, "object" should read --objects--.

Col. 4, line 3, "cyanoundecanoic-cyanoundecanoic" should be deleted.

line 5, after "11-", --cyanoundecanoic-- should be inserted.

Col. 7, line 1, "crystal" should read --crystals--.

line 25, "was" should read --were--.

Signed and Sealed this

Fifteenth Day of January 1980

[SEAL]

Attest:

SIDNEY A. DIAMOND

Attesting Officer

Commissioner of Patents and Trademarks